US011382841B2

(12) United States Patent
Jung et al.

(10) Patent No.: US 11,382,841 B2
(45) Date of Patent: Jul. 12, 2022

(54) MICROSTRUCTURE USING FLUIDIZATION OF SOLID, AND MANUFACTURING METHOD THEREFOR

(71) Applicant: JUVIC INC., Seoul (KR)

(72) Inventors: Hyung Il Jung, Seoul (KR); Hui Suk Yang, Seoul (KR)

(73) Assignee: JUVIC INC., Seoul (KR)

( * ) Notice: Subject to any disclaimer, the term of this patent is extended or adjusted under 35 U.S.C. 154(b) by 0 days.

(21) Appl. No.: 15/744,768

(22) PCT Filed: Jul. 13, 2016

(86) PCT No.: PCT/KR2016/007634
§ 371 (c)(1),
(2) Date: Jan. 13, 2018

(87) PCT Pub. No.: WO2017/010813
PCT Pub. Date: Jan. 19, 2017

(65) Prior Publication Data
US 2018/0200157 A1    Jul. 19, 2018

(30) Foreign Application Priority Data

Jul. 13, 2015  (KR) .................. 10-2015-0099056
Jul. 12, 2016  (KR) .................. 10-2016-0088235

(51) Int. Cl.
| *A61M 5/00* | (2006.01) |
| *A61K 8/02* | (2006.01) |
| *A61K 8/67* | (2006.01) |
| *A61K 8/73* | (2006.01) |
| *A61Q 19/02* | (2006.01) |
| *B81B 1/00* | (2006.01) |
| *B81C 1/00* | (2006.01) |
| *A61K 8/49* | (2006.01) |
| *A61K 9/00* | (2006.01) |

(52) U.S. Cl.
CPC ............ *A61K 8/0204* (2013.01); *A61K 8/498* (2013.01); *A61K 8/676* (2013.01); *A61K 8/735* (2013.01); *A61Q 19/02* (2013.01); *B81B 1/008* (2013.01); *B81C 1/00111* (2013.01); *A61K 9/0021* (2013.01); *B81B 2201/055* (2013.01)

(58) Field of Classification Search
CPC ........ A61M 3/00; A61M 3/0237; A61M 5/00; A61M 5/158; A61M 5/178; A61M 5/3287; A61M 5/3286; A61M 5/3295
See application file for complete search history.

(56) References Cited

U.S. PATENT DOCUMENTS

| 2013/0123707 A1* | 5/2013 | Determan ............ A61K 9/0021 |
| | | 604/173 |
| 2014/0188041 A1* | 7/2014 | Moore ................ A61B 17/205 |
| | | 604/46 |
| 2014/0276589 A1* | 9/2014 | Bayramov ............... A61P 9/12 |
| | | 604/506 |

FOREIGN PATENT DOCUMENTS

| JP | H08-84484 A | 3/1996 | |
| JP | 2009-233170 A | 10/2009 | |
| KR | 10-2012-0006293 A | 1/2012 | |
| KR | 10-2014-0006167 A | 1/2014 | |
| KR | 20140006167 A * | 1/2014 | ........ A61M 37/0015 |
| KR | 10-2014-0051648 A | 5/2014 | |
| WO | WO-2014197995 A1 * | 12/2014 | .......... B81C 1/00111 |

OTHER PUBLICATIONS

International Search Authority/KR, International Search Report dated Oct. 8, 2016 in International Patent Application No. PCT/KR2016/007634 (with English translation), 4 pages.
Sunaina Indermun et al., "Current advances in the fabrication of microneedles for transdermal delivery", Journal of Controlled Release vol. 185 (2014), p. 130-138.

* cited by examiner

*Primary Examiner* — Micah Paul Young
(74) *Attorney, Agent, or Firm* — Sughrue Mion, PLLC

(57) ABSTRACT

The present invention relates to a method of manufacturing a microstructure, including: (a) forming a solid on a substrate; (b) fluidizing the solid by adding a solvent thereto; and (c) shaping the fluidized solid, and a microstructure manufactured using the method.

13 Claims, 11 Drawing Sheets

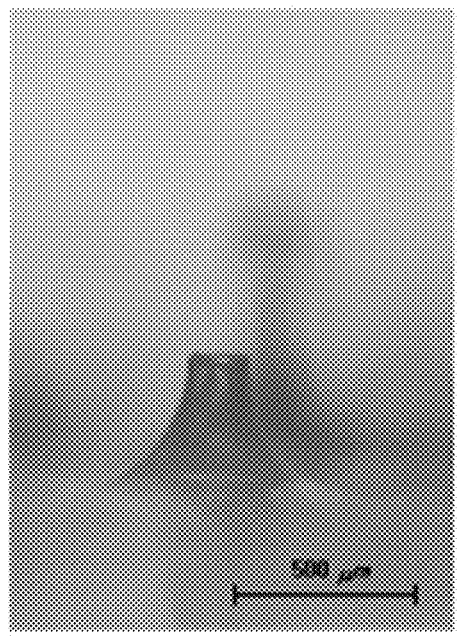 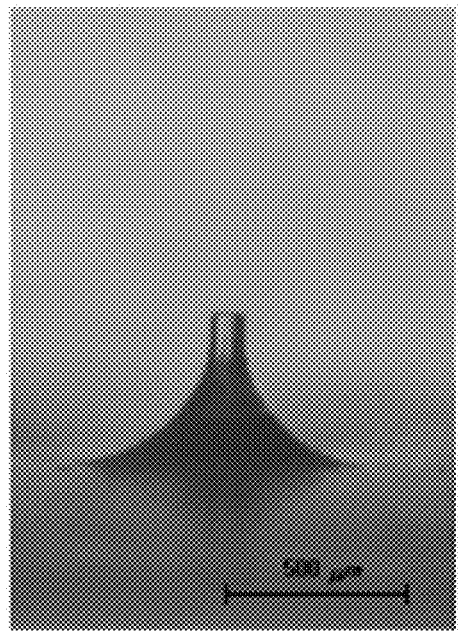
FIG. 15A  FIG. 15B
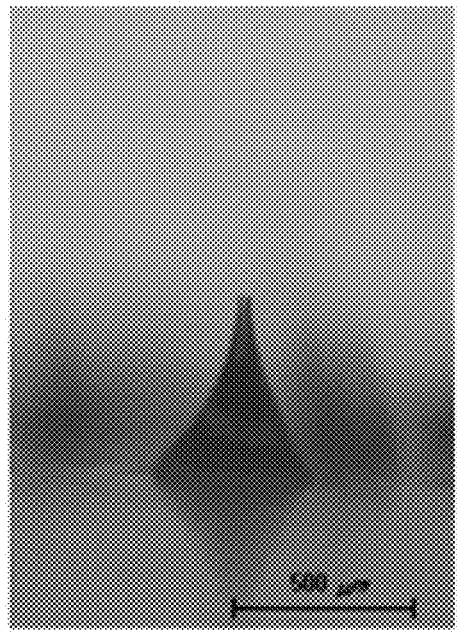
FIG. 15C

MICROSTRUCTURE USING FLUIDIZATION OF SOLID, AND MANUFACTURING METHOD THEREFOR

RELATED APPLICATIONS

This application is the U.S. National Phase of and claims priority to International Patent Application No. PCT/KR2016/007634, International Filing Date Jul. 13, 2016, entitled MICROSTRUCTURE USING FLUIDIZATION OF SOLID, AND MANUFACTURING METHOD THEREFOR; which claims benefit of Korean Patent Application No. 10-2015-0099056 filed Jul. 13, 2015 and Korean Patent Application No. 10-2016-0088235 filed Jul. 12, 2016; both of which are incorporated herein by reference in their entireties.

TECHNICAL FIELD

The present invention relates to a microstructure using fluidization of a solid, and a method of manufacturing the same.

BACKGROUND ART

Currently, several techniques have been developed to deliver drugs into the body. Among these, drug delivery through the skin is performed via forms such as injections, ointments, patches, and the like.

Injection is an effective drug delivery method that rapidly shows the efficacy of a drug by injecting a needle into the body to deliver the drug and by which the drug is directly delivered into internal tissues such as blood or muscles, and thus is used in a variety of fields. However, injections cause strong irritation and tissue damage to the skin, and thus pain occurs. In addition, additional infections may occur due to a wound so that medical procedures can be performed only by an expert.

In the case of ointments or patches, it is difficult to permeate the stratum corneum, and thus this method has limitations in applicable drugs, drug delivery time is long, and it is difficult to deliver a drug in an accurate amount.

To address these problems, microneedles have been devised as a drug delivery system that delivers a drug into the body using a fine needle with minimal invasiveness.

Among the microneedles, biodegradable microneedles refer to a microneedle structure formed of a biodegradable material. A biodegradable material shaped into microneedles passes through the stratum corneum, and is then dissolved by body fluid in the skin and body temperature. At this time, the biodegradable microneedles formed by mixing the biodegradable material with a drug have a principle that loaded drugs are dissolved together and delivered into the body.

Currently, biodegradable microneedles are manufactured by shaping a viscous composition into microneedles. However, the viscosity of the viscous composition is easily changed by the surrounding environment such as humidity and temperature, and thus it is difficult to fabricate a certain form of microneedles when mass-produced. In particular, in a case in which a viscous composition is ejected to form droplets to manufacture biodegradable microneedles, even if the viscous composition is ejected in a certain amount, degrees to which the viscous composition is dried by the surrounding environment vary according to an ejection order, and thus the viscosity of each droplet varies, and thus it is difficult to mass produce uniform biodegradable microneedles. This complicates a precise control process, thus reducing productivity, uniformity, and quality of microneedles.

In addition, the loading of a drug in biodegradable microneedles is performed by, first, preparing a viscous composition by mixing a biodegradable material with a drug and then manufacturing microneedles using the same. However, in the mixing of the biodegradable material with the drug or in a state of a mixed solution of the biodegradable material and the drug, the drug may be denatured or destroyed by the biodegradable material or a solvent. Thus, it is necessary to minimize the interaction between the drug and the solvent or the biodegradable material. When solvents of the biodegradable material and the drug are different from each other, it is possible to form a mixed solution only by addition of a separate surfactant. Due to this, the type of loadable drugs in the biodegradable material is limited. In addition, a mixed solution of the drug and the biodegradable material has a high viscosity, and thus it is difficult to accurately quantify the drug. This is because the drug in the mixed solution becomes non-uniform due to non-uniformity of the biodegradable material. The above-described problems may be regarded as problems occurring due to preparation of and shaping into microneedles only using the mixed solution of the biodegradable material and the drug.

DISCLOSURE

Technical Problem

The present invention provides a method of manufacturing a microstructure, including: (a) forming a solid on a substrate; (b) fluidizing the solid by adding a solvent to the solid; and (c) shaping the fluidized solid.

However, technical problems to be achieved by the present invention are not limited to the above-described technical problems, and other unmentioned technical problems will become apparent from the following description to those of ordinary skill in the art.

Technical Solution

The prevent invention provides a method of manufacturing a microstructure, including: (a) forming a solid on a substrate; (b) fluidizing the solid by adding a solvent thereto; and (c) shaping the fluidized solid.

In process (a), the solid may have a solid content of 70% or more.

In in process (a), the solid may include a separate drug or a separate additive, the separate drug or additive being previously added.

In process (b), the adding may be performed using at least one method selected from the group consisting of contact, ejection, spraying, deposition, and dipping.

In process (b), a degree of fluidization of the solid may be adjusted according to the type of solvent, affinity between the solvent and the solid, an amount of the solvent, or fluidization conditions.

In process (b), the solvent may be added in an amount of 10 parts by volume to 200 parts by volume with respect to 100 parts by weight of the solid.

In a case in which, with respect to a vertical direction of the substrate, the solid is divided into an upper solid layer and a lower solid layer based on a ½ point of the solid, in process (b), a degree of fluidization of the upper solid layer may be higher than a degree of fluidization of the lower solid layer.

In process (b), a drug may be further loaded in the solvent.

The method may further include, after process (b), re-solidifying the fluidized solid and then re-fluidizing the solid by adding a second solvent thereto.

In process (c), the shaping may be performed using at least one method selected from the group consisting of molding, drawing, air-blowing, suction, application of centrifugal force, and application of a magnetic field.

In process (c), the shaping may be performed in such a way that curing simultaneously occurs.

An aspect ratio of the microstructure shaped in process (c) may be adjusted according to a degree of fluidization.

A loading distribution of the drug in the microstructure shaped in process (c) may be adjusted according to a degree of fluidization.

The loading distribution of the drug in the microstructure shaped in process (c) may be adjusted according to a degree of re-fluidization.

According to an embodiment of the present invention, there is provided a microstructure manufactured using the above-described method.

According to another embodiment of the present invention, there is provided a microstructure formed on a substrate and including a drug loaded therein, wherein a loading distribution of the drug in the microstructure forms a gradual concentration gradient.

In a case in which, with respect to a vertical direction of the substrate, the microstructure is divided into an upper microstructure layer and a lower microstructure layer based on a ½ point of the microstructure, a degree of the loading distribution of the drug in the upper microstructure layer may be higher than a degree of the loading distribution of the drug in the lower microstructure layer.

In a case in which, with respect to a vertical direction of the substrate, the microstructure is divided into an upper microstructure layer, an intermediate microstructure layer, and a lower microstructure layer based on ⅓ and ⅔ points of the microstructure, a degree of the loading distribution of the drug in the intermediate microstructure layer may be higher than degrees of the loading distribution of the drug in the upper microstructure layer and the lower microstructure layer.

Advantageous Effects

A method of manufacturing a microstructure using the fluidization of a solid, according to the present invention, can address the difficulty in adjusting the viscosity of a conventional viscous composition, secure the productivity, uniformity, and quality of a microstructure, facilitate mass production of the microstructure, and enable an aspect ratio of the microstructure to be variously adjusted.

In addition, separately from a solid, a drug is additionally loaded in a solvent for the fluidization of the solid, thus facilitating loading of a fixed amount of drug and loading of various preparations of the drug, minimizing a loss in drug activity and enhancing stability, and concentratedly distributing the drug in an upper microstructure layer or an intermediate microstructure layer, which enables the drug to effectively permeate deeply into the skin.

DESCRIPTION OF DRAWINGS

FIG. 15 illustrates optical microscope images showing microstructures according to solvent amounts of 10 μl (a), 15 μl (b), and 20 μl (c), respectively, in Example 2.

BEST MODE

Figure 1:
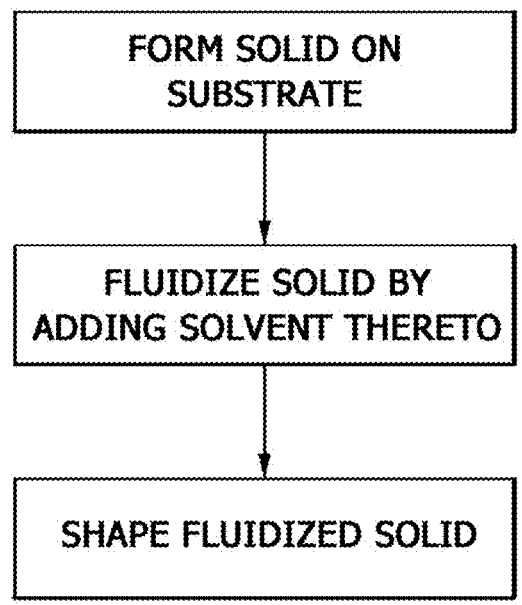
FIG. 1 is a flowchart illustrating a method of manufacturing a microstructure using the fluidization of a solid, according to an embodiment of the present invention.

The inventors of the present invention verified that a microstructure could be successfully manufactured by fluidizing an upper portion of a solid through addition of a solvent to the solid and then shaping the fluidized solid, instead of directly using a viscous composition on a substrate as in existing methods, thus completing the present invention.

Hereinafter, embodiments of the present invention will be described in detail with reference to the accompanying drawings in such a way that the invention may be carried out without undue difficulty by those of ordinary skill in the art to which the invention pertains. The present invention may be embodied in many different forms and is not limited to embodiments described herein.

In the drawings, thicknesses are enlarged to clearly indicate layers and regions. In addition, for convenience of explanation, the thicknesses of some layers and regions are exaggerated in the drawings.

Hereinafter, it will be understood that when an element is referred to as being "on (or below)" a substrate, it can be directly on (or below) the substrate, and it should not be construed as being limited to a configuration where there are no other intervening elements between the substrate and the element thereon (or therebelow).

Hereinafter, the present invention will be described in detail.

The present invention provides a method of manufacturing a microstructure, including: (a) forming a solid on a substrate; (b) fluidizing the solid by adding a solvent to the solid; and (c) shaping the fluidized solid.

Figure 2:
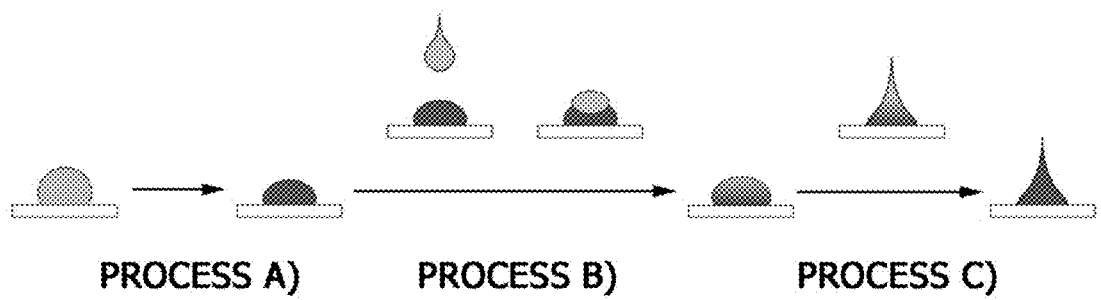
FIG. 2 is a view illustrating the method of manufacturing a microstructure using the fluidization of a solid, according to an embodiment of the present invention.

FIGS. 1 and 2 are a flowchart and view illustrating a method of manufacturing a microstructure using the fluidization of a solid, according to an embodiment of the present invention.

As illustrated in FIGS. 1 and 2, the method of manufacturing a microstructure using the fluidization of a solid, according to an embodiment of the present invention, includes: forming a solid on a substrate (process (a)); fluidizing the solid by adding a solvent to the solid (process (b)); and shaping the fluidized solid (process (c)).

First, the method of manufacturing a microstructure according to the present invention includes forming a solid on a substrate (process (a)).

The substrate is used for final production of a microstructure and used to support the formed solid.

FIG. 3 illustrates the preparation of solids on substrates having various surface shapes.

Figure 3A:
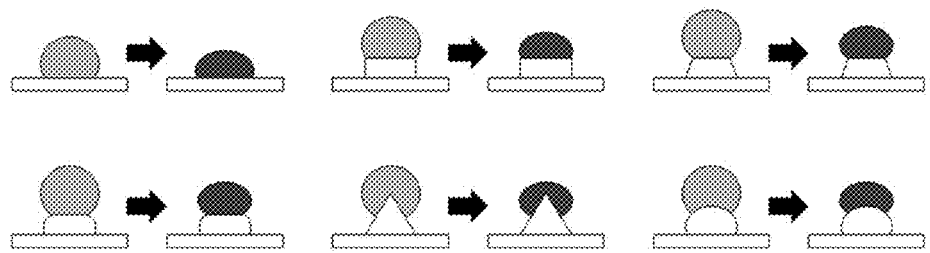
FIG. 3 illustrates the preparation of solids on substrates having various surface shapes.
Figure 3B:
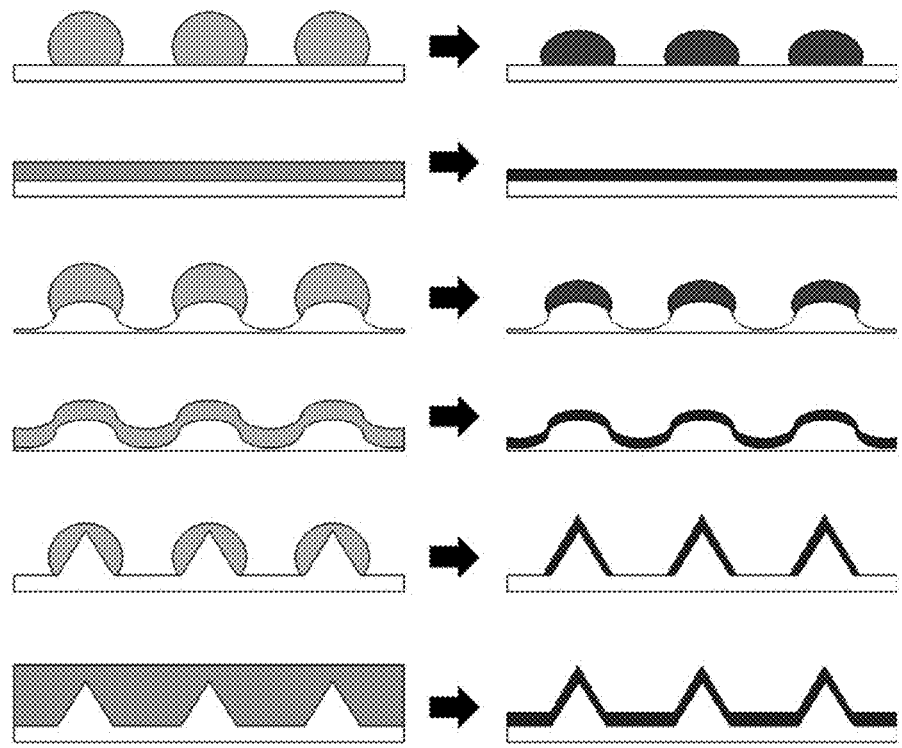

As illustrated in FIG. 3, the substrate may have various surface shapes. In particular, the substrate may be configured to form a single microstructure, and in this case, the substrate may directly support a single solid on the substrate without formation of a pillar, or a single pillar that is used for supporting a single solid and has various shapes such as a cylindrical shape, a truncated conical shape, a conical shape, a hemispherical shape, and the like may be formed on the substrate to thereby adjust a transdermal delivery degree of a microstructure, preferably, a microneedle (see FIG. 3(a)). In addition, the substrate may be configured to form a plurality of microstructures or an integrated microstructure, and in this case, the substrate may directly support a plurality of solids or an integrated solid on the substrate without formation of a pillar, or a curved portion, an uneven portion, or the like having a certain pattern for supporting the plurality of solids or the integrated solid may be formed on the substrate to thereby adjust a transdermal delivery degree of microneedles (see FIG. 3(b)). Such surface shapes of the substrate may be variously selected according to the purpose of use and application forms of the microstructure.

The solid is a concept distinguished from existing viscous compositions, is in a moisture-evaporated state, and the solid may have a solid content of 70% or more, more preferably, 90% or more, but the present invention is not limited thereto. Since the solid content of the solid is maintained within the above range, the solid may be used to address problems due to the difficulty in adjusting the viscosity of an existing viscous composition, thus securing productivity, uniformity, and quality of the microstructure and facilitating mass production thereof.

The solid may be formed through heat or freeze-drying, molding, drawing, air-blowing, centrifugal force, suction, a magnetic field, spraying, electrospinning, and the like of a solid precursor, e.g., by natural drying of viscous droplets ejected onto the substrate or adjustment of pressure, temperature, air-blowing, a magnetic field, electricity, and the like on viscous droplets ejected onto the substrate. In addition, the solid may be formed by applying solid powder to the substrate or transferring a solid previously formed on another substrate to the substrate. In this case, it is preferable that the substrate has higher affinity with the solid than the other substrate.

The solid, which is a polymer material, may include a biocompatible or biodegradable material.

The term "biocompatible material" as used herein refers to a material that is substantially non-toxic to the human body, chemically inert, and non-immunogenic, and the term "biodegradable material" as used herein refers to a material which can be degraded by body fluids, microorganisms, or the like in vivo.

In particular, as the biocompatible or biodegradable material, hyaluronic acid, polyester, polyhydroxyalkanoates (PHAs), poly($\alpha$-hydroxyacid), poly($\beta$-hydroxyacid), poly(3-hydroxybutyrate-co-valerate) (PHBV), poly(3-hydroxyproprionate (PHP), poly(3-hydroxyhexanoate) (PHH), poly(4-hydroxyacid), poly(4-hydroxybutyrate), poly(4-hydroxyvalerate), poly(4-hydroxyhexanoate), poly (esteramide), polycaprolactone, polylactide, polyglycolide, poly(lactide-co-glycolide) (PLGA), polydioxanone, polyorthoester, polyetherester, polyanhydrides, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalates, polyphosphazenes, PHA-PEG, an ethylene vinyl alcohol copolymer (EVOH), polyurethane, silicone, polyester, polyolefins, a copolymer of polyisobutylene and ethylene-$\alpha$-olefin, a styrene-isobutylene-styrene triblock copolymer, acrylic polymers and copolymers, vinyl halide polymers and copolymers, polyvinyl chloride, polyvinyl ether, polyvinyl methyl ether, polyvinylidene halides such as polyvinylidene fluoride and polyvinylidene chloride, polyfluoroalkenes, polyperfluoroalkenes, polyacrylonitrile, polyvinyl ketone, polyvinyl aromatics, polystyrene, polyvinyl esters, polyvinyl acetate, an ethylene-methylmethacrylate copolymer, an acrylonitrile-styrene copolymer, a copolymer of ABS resin and ethylene-vinyl acetate, polyamides, alkyd resins, polyoxymethylene, polyimides, polyether, polyacrylate, polymethacrylate, polyacrylic acid-co-maleic acid, chitosan, dextran, cellulose, heparin, alginate, inulin, starch, or glycogen may be used. Preferably, hyaluronic acid, polyester, polyhydroxyalkanoates (PHAs), poly($\alpha$-hydroxyacid), poly($\beta$-hydroxyacid), poly(3-hydroxybutyrate-co-valerate) (PHBV), poly(3-hydroxyproprionate (PHP), poly(3-hydroxyhexanoate) (PHH), poly(4-hydroxyacid), poly(4-hydroxybutyrate), poly(4-hydroxyvalerate), poly(4-hydroxyhexanoate), poly(esteramide), polycaprolactone, polylactide, polyglycolide, poly(lactide-co-glycolide) (PLGA), polydioxanone, polyorthoester, polyetherester, polyanhydrides, poly(glycolic acid-co-trimethylene carbonate), polyphosphoester, polyphosphoester urethane, poly (amino acid), polycyanoacrylate, poly(trimethylene carbonate), poly(iminocarbonate), poly(tyrosine carbonate), polycarbonate, poly(tyrosine arylate), polyalkylene oxalates, polyphosphazenes, PHA-PEG, chitosan, dextran, cellulose, heparin, alginate, inulin, starch, or glycogen may be used, but the present invention is not limited thereto.

Optionally, a separate drug or a separate additive may be previously added to the solid. As such, the previously added separate drug is characterized by being entirely distributed in the solid, but has limitations in drug loading due to the interaction between the separate drug or the separate additive and a polymer material or a solvent in the solid precursor.

Known drugs may be used as the separate drug, and the separate drug may include, for example, a chemical drug, a protein medicine, a peptide medicine, nucleic acid molecules for gene therapy, nanoparticles, and the like. The separate drug that may be used in the present invention includes, for example, an anti-inflammatory agent, a pain reliever, an anti-arthritic agent, an antispasmodic agent, an antidepressant, an antipsychotic drug, a tranquilizer, an antianxiety drug, a narcotic antagonist, a Parkinson's disease drug, a cholinergic agonist, an anticancer agent, an anti-angiogenesis inhibitor, an immunosuppressant, an antiviral agent, an antibiotic, an anorectic agent, a painkiller, an anticholinergic agent, an antihistaminic agent, an anti-migraine agent, hormones, a coronary, cerebrovascular or peripheral vasodilator, a contraceptive, an antithrombotic, a diuretic, an antihypertensive, a cardiovascular disease drug, beauty care ingredients (e.g., an anti-wrinkle agent, a skin aging inhibitor, and a skin whitening agent), and the like, but the present invention is not limited thereto.

In the present invention, beauty care ingredients, in particular, ascorbic acid 2-glucoside (AA2G), which is a whitening ingredient, is used as the separate drug.

Manufacturing of the microstructure according to the present invention may be performed under non-heating treatment conditions, and thus although the separate drug used in the present invention is a drug susceptible to heat, such as a protein drug, a peptide drug, nucleic acid molecules for genetic treatment, vitamins (preferably, vitamin C), and the like, according to the present invention, it is possible to manufacture a microstructure including the separate drug.

The protein/peptide drug include a hormone, a hormone analogue, an enzyme, an enzyme inhibitor, a signal transduction protein or a fragment thereof, an antibody or a fragment thereof, a single chain antibody, a binding protein or a binding domain thereof, an antigen, an adhesive protein, a structural protein, a regulatory protein, a toxin protein, a cytokine, a transcription factor, a blood coagulation factor, and a vaccine, but the present inventions not limited thereto. More particularly, the protein/peptide drug may include insulin, insulin-like growth factor 1 (IGF-1), growth hormones, erythropoietin, granulocyte-colony stimulating factors (G-CSFs), granulocyte/macrophage-colony stimulating factors (GM-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptitibatide, growth hormone releasing hormone-II II), gonadorelin, guserelin, histrelin, leuprorelin, lypressin, octreotide, oxytocin, pitressin, secretin, sincalide, terlipressin, thymopentin, thymosine α1, triptorelin, bivalirudin, carbetocin, cyclosporine, exedine, lanreotide, luteinizing hormone-releasing hormone (LHRH), nafarelin, parathyroid hormone, pramlintide, enfuvirtide (T-20), thymalfasin, and ziconotide.

The separate additive mainly refers to various materials for enhancing an effect or stability of the separate drug, and, as the separate additive, known immunity inducers for increasing the efficacy of the drug, saccharides such as trehalose for enhancing the stability of the drug, or the like may be used. In addition, energy may also be used. In this case, the microstructure may be used for transfer or transmission of an energy form such as thermal energy, light energy, electrical energy, or the like.

For example, in photodynamic therapy, the microstructure may be used to induce light to a specific site inside the body so as to allow light to directly act on the tissue or allow light to act on a mediator such as light-sensitive molecules.

In particular, an amount of the separate drug or the separate additive may range from 0.1 part by weight to 10 parts by weight with respect to 100 parts by weight of the biocompatible or biodegradable material, but the present invention is not limited thereto.

FIG. 4 illustrates the preparation of solids using various methods.

Figure 4A:
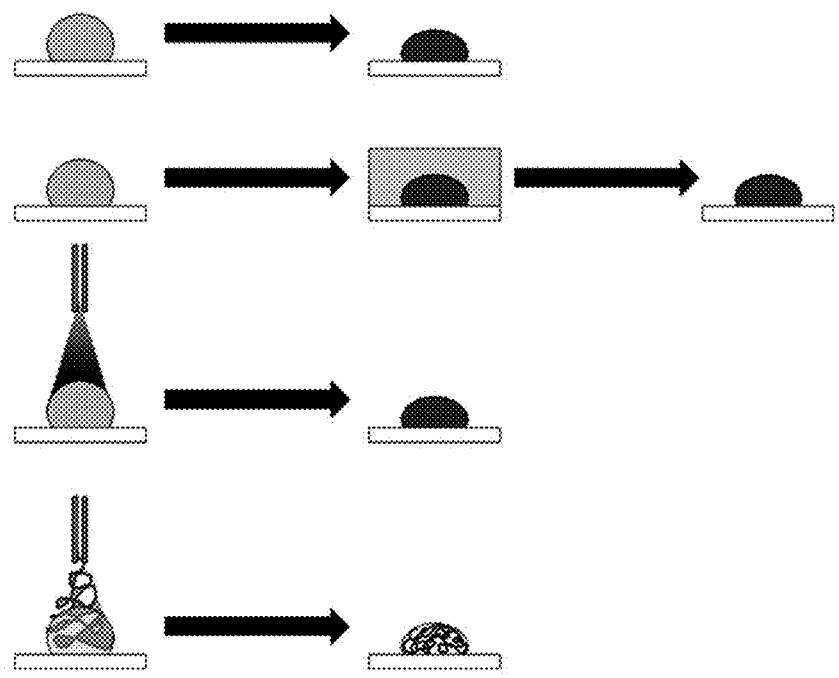
FIG. 4 illustrates the preparation of solids using various methods.
Figure 4B:
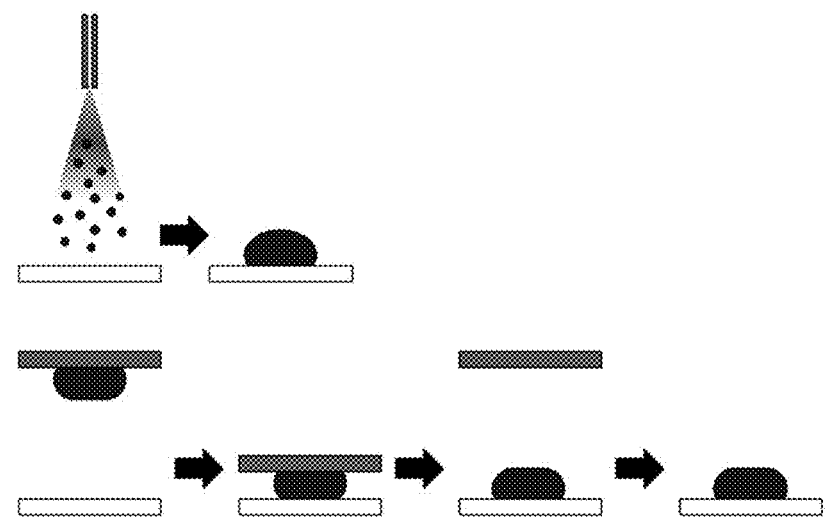

As illustrated in FIG. 4(a), the solid may be formed on the substrate sequentially through natural drying, molding, spraying, and electrospinning of viscous droplets, and, as illustrated in FIG. 4(b), the solid may be formed sequentially by applying solid powder to the substrate and transferring a solid previously formed on another substrate thereto.

Figure 4C:
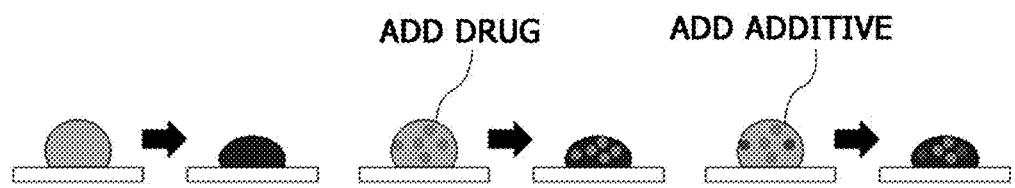

In addition, as illustrated in FIG. 4(c), the separate drug or additive may not be previously added to the solid, the separate drug may be previously added to the solid by adding the separate drug to the solid precursor, or the separate additive may be previously added to the solid by previously adding the separate additive to the solid precursor.

Figure 5:
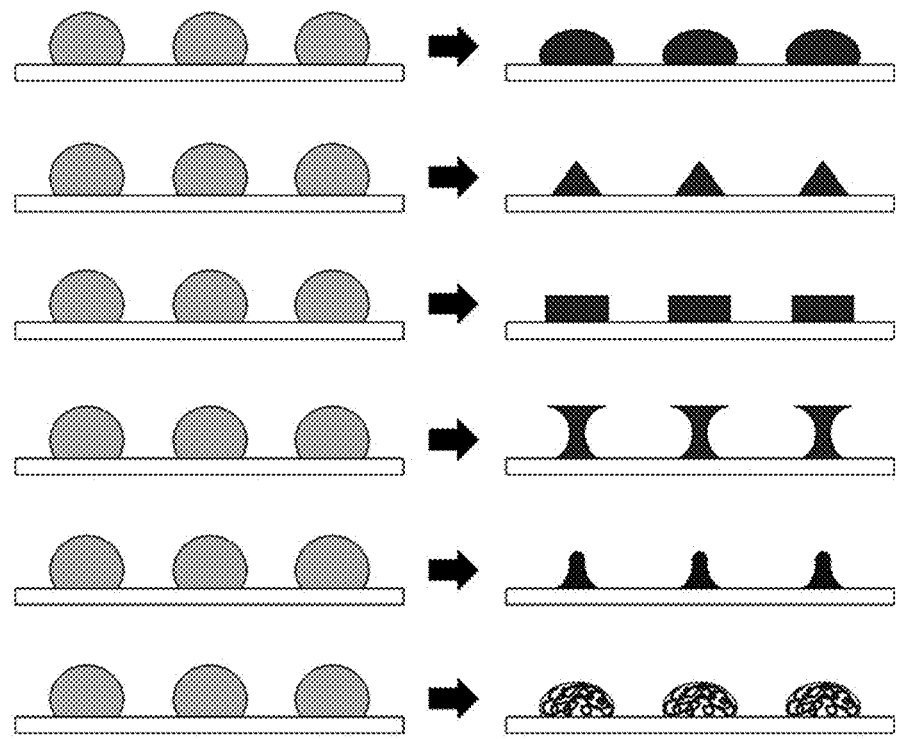
FIG. 5 illustrates solids having various shapes.

FIG. 5 illustrates solids having various shapes.

As illustrated in FIG. 5, the solid may be formed in various shapes by using the above-described various methods, and microstructures having various shapes may be finally produced from the solids having various shapes, and thus drug loading distribution, a degree of drug delivery, and the like may be adjusted.

Next, the method of manufacturing a microstructure according to the present invention includes fluidizing the solid by adding a solvent to the solid (process (b)).

Various known solvents may be used as the solvent used in the fluidizing process. In particular, as the solvent, a polar solvent such as water, a lower alcohol having 1 to 4 carbon atoms, or the like may be used, or a nonpolar solvent such as hexane, acetone, chloroform, dichloromethane, ethyl acetate, or the like may be used.

Addition of the solvent may be performed using a method known in the art, and may be performed using at least one method selected from the group consisting of contact, ejection, spraying, deposition, and dipping, but the present invention is not limited thereto. At this time, in a case in which the addition of the solvent is performed using a method via contact, when a plurality of solids are formed on the substrate, the plurality of solids may be fluidized using a separate substrate on which the solvent is completely or partially applied. Meanwhile, when an integrated solid is formed on the substrate, the integrated solid may be partially fluidized using a separate substrate on which the solvent is partially applied or a separate substrate having a plurality of pillars on which the solvent is applied.

Figure 6:
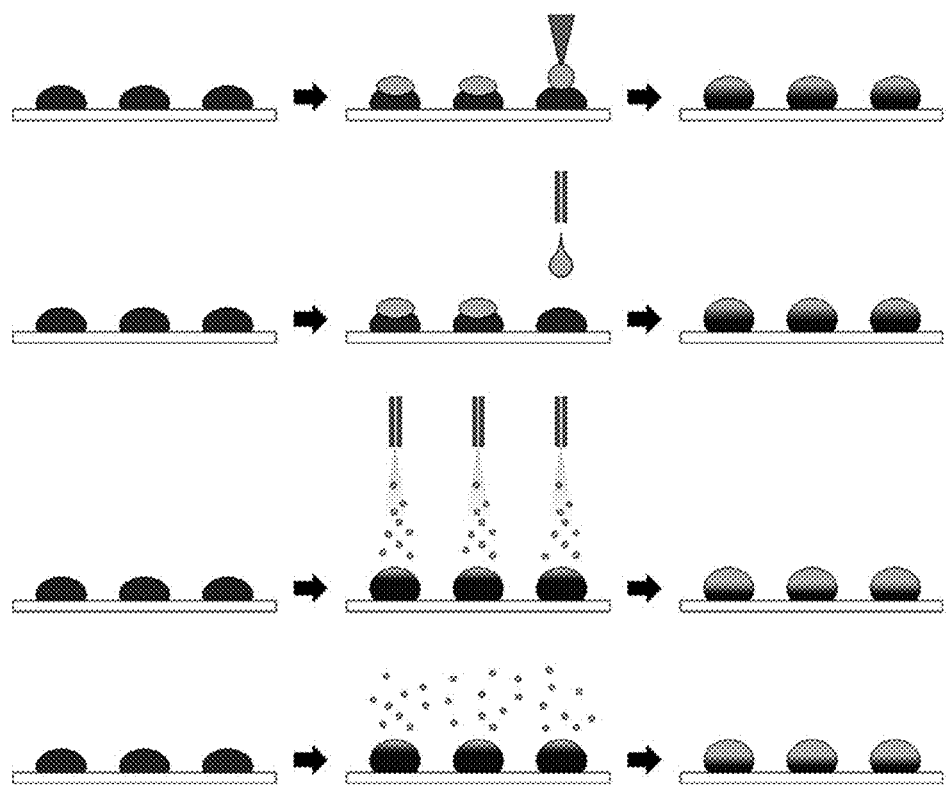
FIG. 6 illustrates the addition of a solvent to a solid using various methods and fluidization of the solid.

FIG. 6 illustrates the addition of a solvent to a solid using various methods and fluidization of the solid.

As illustrated in FIG. 6, the addition of the solvent may be performed using methods such as ejection-contact, ejection via a jet nozzle, spraying via jet nozzles, and deposition.

Figure 7:
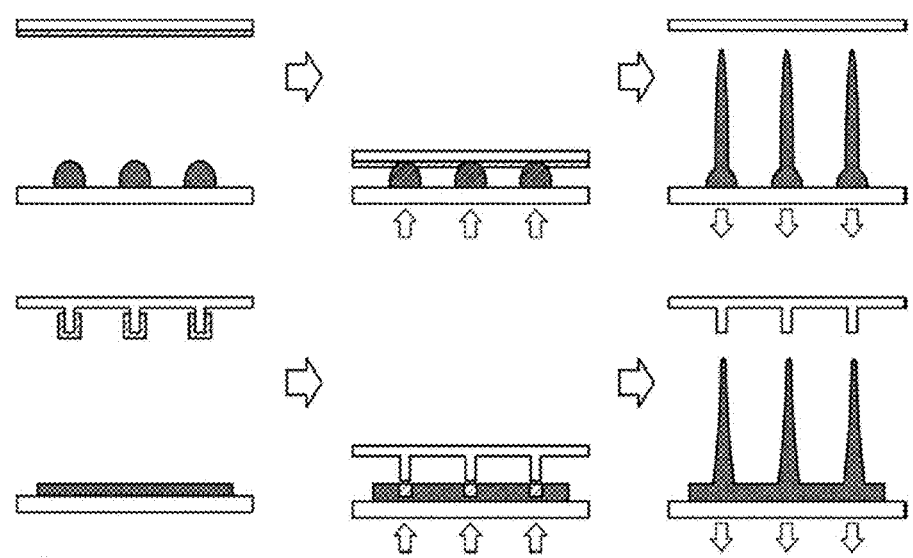
FIG. 7 illustrates the addition of a solvent to a solid using a separate substrate and fluidization of the solid.

FIG. 7 illustrates the addition of a solvent to a solid using separate substrates and fluidization of the solid.

As illustrated in FIG. 7, the addition of the solvent may be performed using a separate substrate on which the solvent is applied and a separate substrate having a plurality of pillars on which the solvent is applied.

In addition, the degree of fluidization of the solid may be adjusted according to the type of solvent, affinity between the solvent and the solid, the amount of solvent, or fluidization conditions.

The term "the degree of fluidization" as used herein refers to a content of the solvent in the solid, and a smaller solid content and a greater solvent content in the solid may be considered to indicate a greater degree of fluidization.

In particular, in the case of high affinity between the solvent and the solid, although other conditions are maintained, the solvent may relatively deeply permeate into the solid, thus increasing the degree of fluidization. In contrast, in the case of low affinity between the solvent and the solid, although other conditions are maintained, the solvent may relatively shallowly permeate into the solid, thus decreasing the degree of fluidization.

For example, when a polar solvent is used as the solvent, the polar solvent easily permeates into a hydrophilic polymer-containing solid, and thus the degree of fluidization is increased, while being unable to easily permeate into a hydrophobic polymer-containing solid, and thus the degree of fluidization is decreased. In contrast, when a nonpolar solvent is used as the solvent, this case shows a tendency opposite to the above case.

At this time, the degree of fluidization may be precisely adjusted according to the permittivity of the polar solvent or the nonpolar solvent.

That is, the higher the affinity between the solvent and the solid, the deeper the solvent permeates into the solid, which results in a greater degree of fluidization, and thus a microstructure with a high aspect ratio may be finally produced. In contrast, the lower the affinity between the solvent and the solid, the shallower the solvent permeates into the solid, which results in a smaller degree of fluidization, and thus a microstructure with a small aspect ratio may be finally produced.

In addition, as the amount of the solvent is increased, the solvent may permeate into the solid more deeply, which results in an increased degree of fluidization, and thus a microstructure with a high aspect ratio may be manufactured. In contrast, when the amount of the solvent is decreased, the solvent may permeate into the solid more shallowly, which results in a decreased degree of fluidization, and thus a microstructure with a low aspect ratio may be manufactured.

In particular, in process (b) above, the solvent is added in an amount of 10 parts by volume to 200 parts by volume, preferably, 30 parts by volume to 200 parts by volume, with respect to 100 parts by weight of the solid, and thus the degree of fluidization is appropriately adjusted, and, accordingly, a microstructure with an appropriate aspect ratio may be manufactured.

In addition, after addition of the solvent, the degree of fluidization may be adjusted by controlling fluidization conditions such as fluidization temperature, fluidization humidity, fluidization time, and the like.

FIG. 8 illustrates the degree of fluidization adjusted according to affinity between a solvent and a solid (a), the amount of the solvent (b), and fluidization time (c).

Figure 8A:
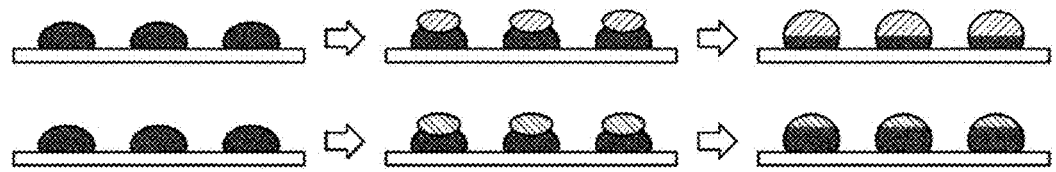
FIG. 8 illustrates the degree of fluidization adjusted according to affinity between a solvent and a solid (a), the amount of the solvent (b), and fluidization time (c).

As illustrated in FIG. 8(a), the case of high affinity between the solvent and the solid (first image) exhibits a relatively high degree of fluidization, and the case of low affinity between the solvent and the solid (second image) exhibits a relatively low degree of fluidization.

Figure 8B:
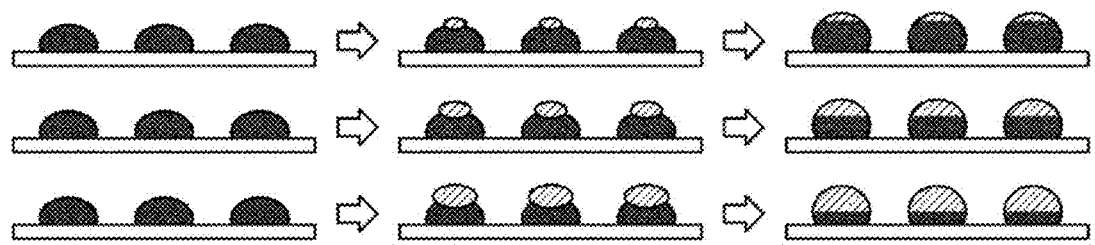
Figure 8C:
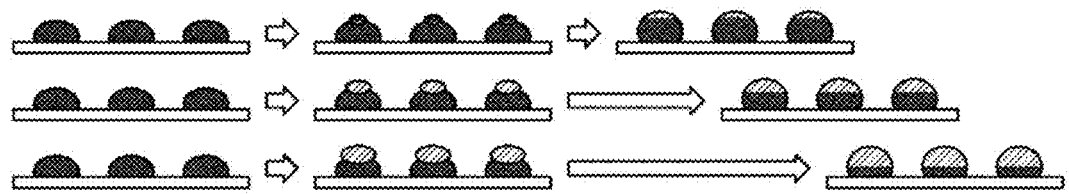

As illustrated in FIG. 8(b), the larger the amount of the solvent, the higher the degree of fluidization, and as illustrated in FIG. 8(c), the longer the fluidization time, the higher the degree of fluidization.

In a case in which, with respect to a vertical direction of the substrate, the solid is divided into an upper solid layer and a lower solid layer based on the ½ point of the solid, it is characterized that the degree of fluidization of the upper solid layer is higher than that of the lower solid layer, and thus shaping thereof is facilitated, and, accordingly, a microstructure having a sharp upper end portion may be finally produced, enabling the microstructure to have a shape suitable for use as a microneedle.

The expression "the ½ point of the solid" as used herein refers to a midpoint of the solid between the lowest point of a surface of the substrate, contacting a lower end portion of the solid and the upper end portion of the solid, with respect to the vertical direction of the substrate.

Meanwhile, by forming a viscous composition by adding a polymer material such as a biocompatible or biodegradable material to the solvent, the aspect ratio of the microstructure may be precisely adjusted.

As described above, the solvent may be added to the solid, or a drug-loaded solvent may be added to the solid. Separately from the solid, a drug may be separately further loaded in the solvent for fluidization of the solid, and thus loading of the drug in a fixed amount and loading of various preparations of the drug may be facilitated, a loss in drug activity may be minimized, and stability of the drug may be enhanced.

As the drug, the same type as that of the above-described separate drug may be used, and the drug may not be particularly limited in terms of type, dose, preparation, and the like. Also, an additive may also be further loaded in the solvent. In the present invention, as the drug, beauty care ingredients, in particular, ascorbic acid 2-glucoside (AA2G), which is a whitening ingredient, is used.

In particular, the amount of the drug may range from 0.1 part by weight to 10 parts by weight with respect to 100 parts by volume of a solution (the drug (additive) and the solvent), but the present invention is not limited thereto.

Figure 9:
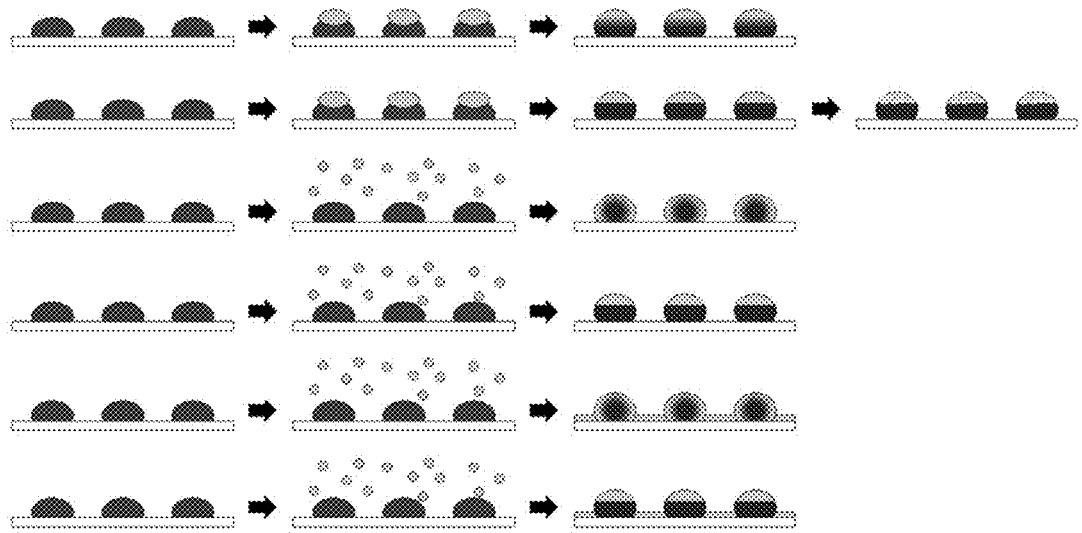
FIG. 9 illustrates the addition of a drug-loaded solvent to a solid using various methods and fluidization of the solid.

FIG. 9 illustrates the addition of a drug-loaded solvent to a solid using various methods and fluidization of the solid.

As illustrated in FIG. 9, the addition of the drug-loaded solvent to the solid and fluidization of the solid may be performed through ejection and natural drying, ejection and freeze-drying, omnidirectional deposition in the solid, deposition in an upper end of the solid, omnidirectional deposition in the solid and support surface deposition, and deposition in the upper end of the solid and support surface deposition.

Figure 10A:
FIG. 10 illustrates the loading distribution of a drug in a solid according to the degree of fluidization adjusted according to a difference of the solubility between a drug-loaded solvent and a solid (a) and fluidization time (b).
Figure 10B:
Figure 10B:
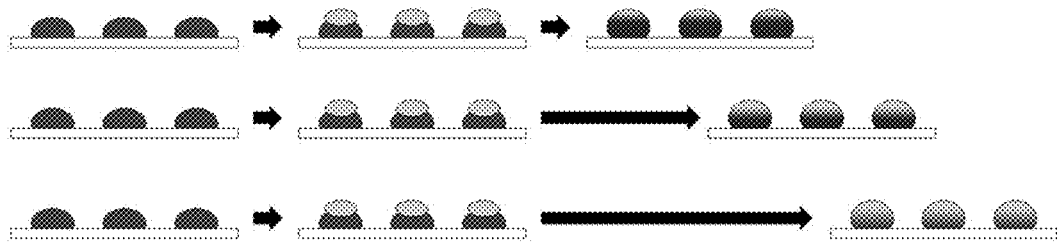

FIG. 10 illustrates the loading distribution of a drug in a solid according to the degree of fluidization adjusted according to a difference of the solubility between a drug-loaded solvent and a solid (a) and fluidization time (b).

As illustrated in FIG. 10(a), in a case in which the solid has a high solubility in the drug-loaded solvent (first image), the degree of fluidization is relatively high, and in a case in which the solid has a low solubility in the drug-loaded solvent (second image), the degree of fluidization is relatively low.

As illustrated in FIG. 10(b), as fluidization time is increased, the degree of fluidization becomes higher, and the loading distribution of the drug in the solid becomes wider.

In addition, the solid may be fluidized by adding a drug-further loaded solvent thereto and the fluidized solid may be directly shaped, or the solid may be fluidized by adding a drug-further loaded solvent thereto, followed by re-solidification of the fluidized solid, and then the solid may be re-fluidized by adding a second solvent thereto to be shaped. As such, when re-solidifying and re-fluidizing processes are further performed, the loading distribution of the drug may be more freely adjustable.

At this time, by forming a viscous composition by adding a polymer material such as a biocompatible or biodegradable material to the second solvent, the loading distribution of the drug may be concentrated in an intermediate layer of the microstructure.

The second solvent may be identical to or different from the above-described solvent. An additional drug or an additional additive may also be further loaded in the second solvent.

Figure 11:
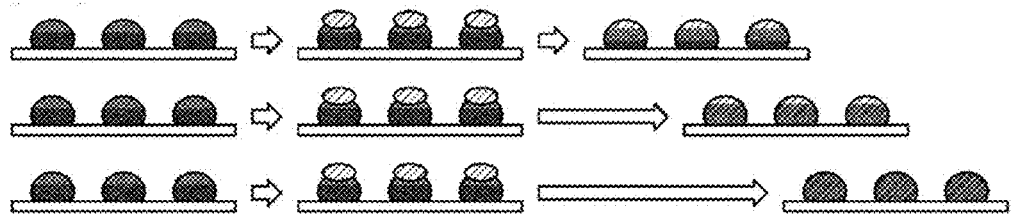
FIG. 11 illustrates the degree of re-fluidization adjusted according to re-fluidization time and the loading distribution of a drug in a re-solidified product.

FIG. 11 illustrates the degree of re-fluidization adjusted according to re-fluidization time and the loading distribution of a drug in a re-solidified product.

As illustrated in FIG. 11, as fluidization time is increased, the degree of re-fluidization due to the second solvent becomes higher, and the loading distribution of the drug in the re-solidified product gradually becomes wider.

Figure 12:
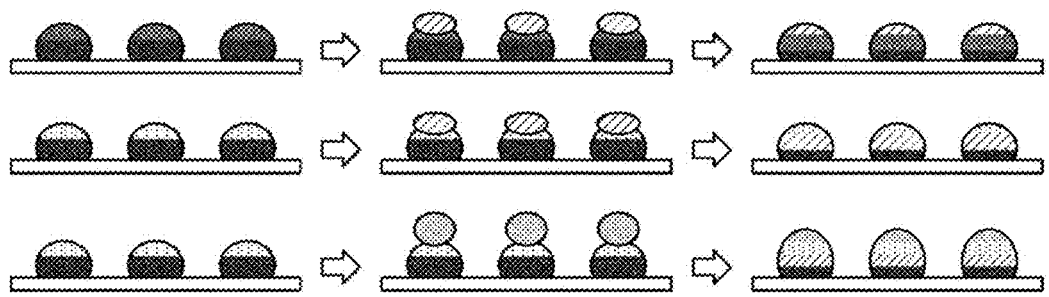
FIG. 12 is a view illustrating the degree of re-fluidization adjusted according to a difference of the solubility among a drug-loaded solvent, a solid and a second solvent and the loading distribution of a drug in a re-solidified product.

FIG. 12 is a view illustrating the degree of re-fluidization adjusted according to a difference of the solubility among a drug-loaded solvent, a solid and a second solvent and the loading distribution of a drug in a re-solidified product.

As illustrated in FIG. 12, in a case in which the solid has a high solubility in the drug-loaded solvent, when a second solvent having a high solubility with respect to the drug is added (first image), the loading distribution of the drug in the solid becomes wider due to the second solvent. In addition, in a case in which the solid has a low solubility in the drug-loaded solvent, when a second solvent having a low solubility with respect to the drug is added (second image), the loading distribution of the drug in the re-solidified product becomes relatively narrow.

In addition, in a case in which the solid has a low solubility in the drug-loaded solvent, when a second solvent with a polymer material added thereto is added (third image), a polymer material layer is formed on a drug loading distribution layer in the re-solidified product, and thus the loading distribution of the drug is in an intermediate layer of the finally produced microstructure.

Lastly, the method of manufacturing a microstructure according to the present invention may include shaping the fluidized solid (process (c)).

In process (c), the shaping may be performed using a molding method, or may be performed by applying an outward force to the fluidized solid using at least one method selected from the group consisting of drawing, air-blowing, suction, the application of centrifugal force, and the application of a magnetic field. At this time, the shaping may be performed such that curing simultaneously occurs.

The aspect ratio of the shaped microstructure may be adjusted according to the degree of fluidization.

The expression "aspect ratio of the microstructure" as used herein refers to a ratio of the height of the microstructure from the lowest point of the surface of the substrate, contacting the lower end portion of the solid in a vertical direction of the substrate to the upper end portion of the microstructure with respect to a maximum diameter, when the microstructure is cut in a horizontal direction of the substrate.

That is, the aspect ratio of the microstructure refers to a ratio of height to maximum diameter of the microstructure, and as the degree of fluidization is higher, a contraction rate is increased during shaping, and thus the aspect ratio of the microstructure tends to increase.

Meanwhile, when the solid is fluidized or re-fluidized by adding a drug-loaded solvent thereto, the loading distribution of a drug in the shaped microstructure may be adjusted according to the degree of fluidization or re-fluidization.

FIG. 13 illustrates the loading distribution of a drug, adjusted according to: an aspect ratio of the microstructure adjusted according to the degree of fluidization (a); and the degree of re-fluidization (b).

Figure 13A:
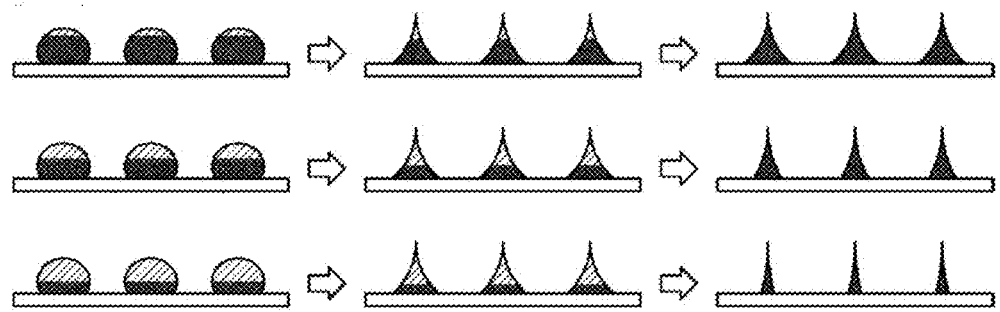
FIG. 13 illustrates the loading distribution of a drug in a microstructure, adjusted according to: an aspect ratio of the microstructure adjusted according to the degree of fluidization (a); and the degree of re-fluidization (b).
Figure 13B:
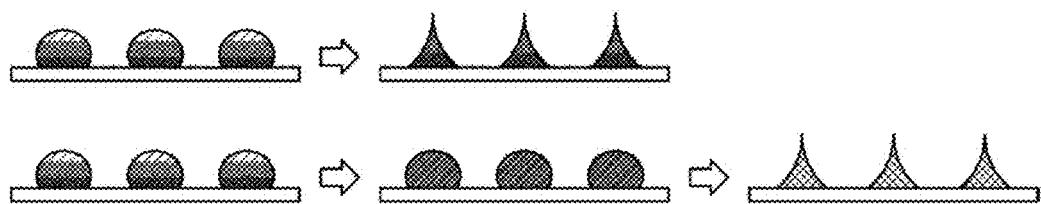

As illustrated in FIG. 13(a), as the degree of fluidization becomes higher, the contraction rate is increased during shaping, and thus the aspect ratio of the microstructure tends to increase. In addition, as illustrated in FIG. 13(b), as in the first or second image of FIG. 11, in the case of a low degree of re-fluidization, the drug is not distributed in the lower microstructure layer, but may be concentratedly distributed in the upper microstructure layer. In contrast, as in the third image of FIG. 11, in the case of a high degree of re-fluidization, the drug may be entirely distributed in the microstructure.

That is, the aspect ratio of the microstructure may be adjusted according to the degree of fluidization of the solid, and the loading distribution of a drug in the microstructure may be adjusted according to the degree of re-fluidization of the re-solidified product.

The present invention also provides a microstructure manufactured according to the method.

The present invention also provides a microstructure formed on a substrate and having a drug loaded therein, wherein the loading distribution of a drug in the microstructure forms a gradual concentration gradient.

The loading distribution of a drug in the microstructure may form a gradual concentration gradient due to the degree of fluidization.

In a case in which, with respect to a vertical direction of the substrate, the microstructure is divided into an upper microstructure layer and a lower microstructure layer based on the ½ point of the microstructure, it may be characterized that a degree of the loading distribution of a drug in the upper microstructure layer is higher than a degree of the loading distribution of the drug in the lower microstructure layer.

Such a microstructure may be manufactured by addition of a drug-loaded solvent, fluidization, and then directly performing shaping, or through addition of a drug-loaded solvent, fluidization, re-solidification, re-fluidization, and then shaping. The microstructure manufactured by the above-described processes may be concentratedly distributed in the upper microstructure layer so that the drug can effectively permeate deeply into the skin.

In addition, in a case in which, with respect to a vertical direction of the substrate, the microstructure is divided into an upper microstructure layer, an intermediate microstructure layer, and a lower microstructure layer based on the ⅓ and ⅔ points of the microstructure, it may be characterized that a degree of the loading distribution of a drug in the intermediate microstructure layer is higher than degrees of the loading distribution of the drug in the upper microstructure layer and the lower microstructure layer.

Such a microstructure may be manufactured through addition of a drug-loaded solvent, fluidization, re-solidification, re-fluidization using a polymer material-containing second solvent, and then shaping, and in the microstructure manufactured by the above-described processes, the drug may be concentratedly distributed in the intermediate microstructure layer so that the drug can effectively permeate into an appropriate position of the skin.

The microstructure according to the present invention may be used in a form of, in addition to a microneedle, a microblade, a microknife, a microfiber, a microspike, a microprobe, a microbarb, a microarray, a microelectrode, or the like.

Thus, the method of manufacturing a microstructure using fluidization of a solid, according to the present invention, may address the difficulty in adjusting the viscosity of a conventional highly-viscous composition, secure productivity, uniformity, and quality of the microstructure, facilitate mass production of the microstructure, and may enable the aspect ratio of the microstructure to be variously adjusted.

In addition, separately from a solid, a drug is additionally loaded in a solvent for the fluidization of the solid, thus facilitating loading of a fixed amount of drug and loading of various preparations of the drug, minimizing a loss in drug activity and enhancing stability, and concentratedly distributing the drug in an upper microstructure layer, which enables the drug to effectively permeate deeply into the skin.

Hereinafter, exemplary embodiments will be described to aid in understanding the present invention. However, the following examples are provided only for more easy understanding of the present invention and are not intended to limit the content of the present invention.

EXAMPLES

Example 1

A solution including 55 (w/v) % of hyaluronic acid (29 kDa) and 0.1 (w/v) % of rhodamine B as a red pigment was ejected onto a stainless steel substrate by applying a pressure of 200 kPa thereto for 0.110 seconds through a dispenser (Musashi, ML-5000X-mini), and then naturally dried to form a solid in a state in which moisture was mostly evaporated (solid content=98%). 60 µl of distilled water was ejected onto 50 µg of the formed solid by using a jet nozzle, and then the solid was fluidized at 23° C. and 50% humidity for 30 seconds. Subsequently, to shape the fluidized solid, the substrate was mounted on a centrifuge (Combi-514R), and the centrifuge was accelerated to 11.6 g/sec, and then operated at a gravitational acceleration of 900 g for 3 minutes. Thereafter, the centrifuge was decelerated at a rate of 14.3 g/sec to thereby complete the manufacture of a microstructure. At this time, curing simultaneously occurred in a shaping process.

Figure 14A:
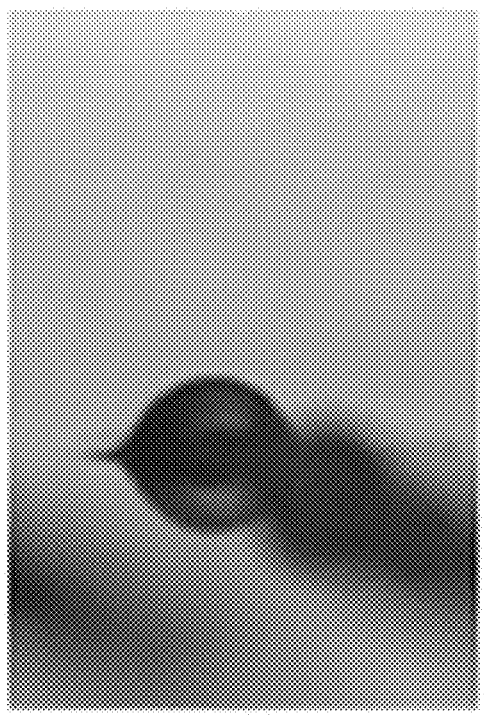
FIG. 14 illustrates optical microscope images respectively showing a solid (a) and a microstructure (b) in Example 1.
Figure 14B:
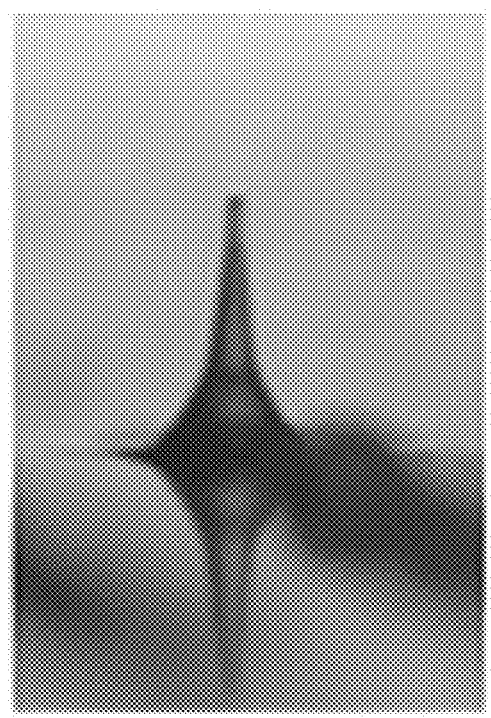

FIG. 14 illustrates optical microscope images respectively showing a solid (a) and a microstructure (b) in Example 1.

As illustrated in FIG. 14, as a result of observing a solid (a) and a microstructure (b) through an optical microscope (SC-150, Samwon, Korea), it was confirmed that the microstructure could be successfully manufactured by fluidizing the solid and then shaping the fluidized solid.

Example 2

A solution including 60 (w/v) % of hyaluronic acid (30 kDa) and 0.1 (w/v) % of rhodamine B as a red pigment was ejected onto an aluminum substrate by applying a pressure of 200 kPa thereto for 0.110 seconds through a dispenser (Musashi, ML-5000X-mini), and then naturally dried to form a solid in a state in which moisture was mostly evaporated (solid content=99.9%). Distilled water was ejected in each of amounts of 10 µl, 15 µl, and 20 µl onto 50 µg of the formed solid by using a jet nozzle, and then the solid was fluidized at 23° C. and 50% humidity for 30 seconds. Subsequently, to shape the fluidized solid, the substrate was mounted on a centrifuge (Combi-514R), and the centrifuge was rotated at 2,700 rpm for 1 minute to thereby complete the manufacture of a microstructure. At this time, curing simultaneously occurred in a shaping process.

FIG. 15 illustrates optical microscope images showing microstructures according to solvent amounts of 10 µl (a), 15 µl (b), and 20 µl (c), respectively, in Example 2.

As illustrated in FIG. 15, it can be seen that, as the amount of the solvent is increased, the solvent can deeply permeate into the solid, and thus the degree of fluidization is increased, and, accordingly, a microstructure with a high aspect ratio may be manufactured, whereas, as the amount of the solvent is decreased, the solvent can shallowly permeate into the solid, and thus the degree of fluidization is decreased, and, accordingly, a microstructure with a low aspect ratio may be manufactured. Thus, it may be considered that an appropriate degree of fluidization is adjustable by adding, to the solid, the solvent in an amount of 10 parts by volume to 40 parts by volume, preferably, 15 parts by volume to 40 parts by volume, with respect to 100 parts by weight of the solid.

Example 3

A solution including 2 (w/v) % of ascorbic acid 2-glucoside (AA2G) as a whitening ingredient, 60 (w/v) % of hyaluronic acid (30 kDa), and 0.1 (w/v) % of rhodamine B as a red pigment was ejected onto an aluminum substrate by applying a pressure of 200 kPa thereto for 0.110 seconds through a dispenser (Musashi, ML-5000X-mini), and then naturally dried to form a solid in a state in which moisture was mostly evaporated (solid content=99.9%). 20 µl of distilled water was ejected onto 50 µg of the formed solid by using a jet nozzle, and then the solid was fluidized at 23° C. and 50% humidity for 30 seconds. Subsequently, to shape the fluidized solid, the substrate was mounted on a centrifuge (Combi-514R), and the centrifuge was rotated at 2,700 rpm for 1 minute to thereby complete the manufacture of a microstructure. At this time, curing simultaneously occurred in a shaping process.

Figure 16A:
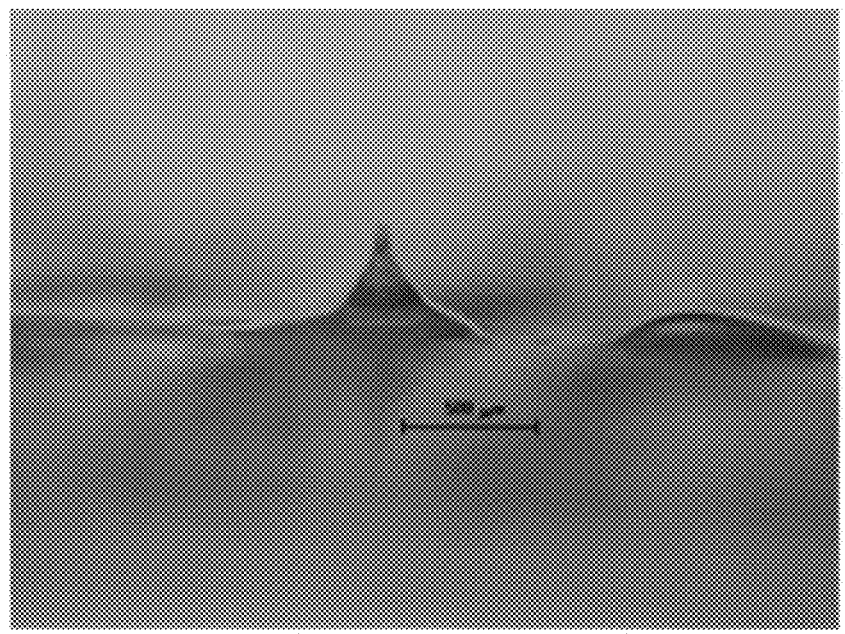
FIG. 16 illustrates optical microscope images respectively showing a microstructure of Example 3 (a) and a microstructure of Example 4 (b).

FIG. 16(a) is an optical microscope image showing the microstructure of Example 3, and it was confirmed that the microstructure could be successfully manufactured by fluidizing a solid to which a separate drug was previously added and then shaping the fluidized solid.

Example 4

A solution including 60 (w/v) % of hyaluronic acid (30 kDa) and 0.1 (w/v) % of rhodamine B as a red pigment was ejected onto an aluminum substrate by applying a pressure of 200 kPa thereto for 0.110 seconds through a dispenser (Musashi, ML-5000X-mini), and then naturally dried to form a solid in a state in which moisture was mostly evaporated (solid content=99.9%). 20 µl of a solution including 2 (w/v) % of ascorbic acid 2-glucoside (AA2G) as a whitening ingredient and distilled water was ejected onto 50 µg of the formed solid by using a jet nozzle, and then the solid was fluidized at 23° C. and 50% humidity for 30 seconds. Subsequently, to shape the fluidized solid, the substrate was mounted on a centrifuge (Combi-514R), and the centrifuge was rotated at 2,700 rpm for 1 minute to thereby complete the manufacture of a microstructure. At this time, curing simultaneously occurred in a shaping process.

Figure 16B:
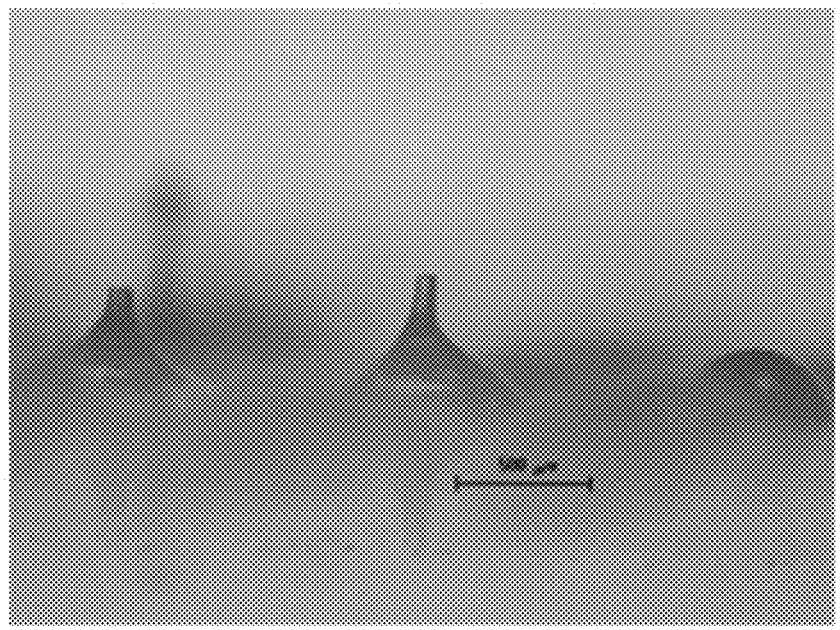

FIG. 16(b) is an optical microscope image showing the microstructure of Example 4, and it was confirmed that the microstructure could be successfully manufactured by fluidizing the solid with a drug-further loaded solvent and then shaping the fluidized solid.

The foregoing description of the present invention is provided for illustrative purposes only, and it will be understood by those of ordinary skill in the art to which the present invention pertains that the present invention may be easily modified in other particular forms without changing the technical spirit or essential characteristics of the present invention. Thus, the embodiments described herein should be construed as being provided for illustrative purposes only and not for purposes of limitation.

The invention claimed is:

1. A method of manufacturing a microstructure, the method comprising, in this order:
   (a) forming a solid of a first shape on a surface of a substrate, wherein the solid comprises a biocompatible or biodegradable material and the substrate surface is smooth or has a protrusion;
   (b) dissolving a portion of the solid of the substrate prepared in process (a) by adding a solvent thereto to fluidize the portion of the solid; and
   (c) shaping the fluidized solid obtained in process (b) to give the microstructure of a second shape, said second shape being different from the first shape and having an aspect ratio different from that of the first shape;
   wherein in process (a), the solid has a solid content of 70% or more and in process (b) dissolving the portion of the solid is performed separately after the solid is formed on the substrate and in a case in which, with respect to a vertical direction of the substrate, the solid is divided into an upper solid layer and a lower solid layer based on a ½ point of the solid, in process (b), a degree of fluidization of the upper solid layer is higher than a degree of fluidization of the lower solid layer.

2. The method of claim 1, wherein in process (a), the solid comprises a separate drug or a separate additive, the separate drug or additive being previously added.

3. The method of claim 1, wherein in process (b), the adding is performed using a method selected from the group consisting of contact, ejection, spraying, deposition, dipping, and a combination thereof.

4. The method of claim 1, wherein in process (b), a degree of fluidization of the solid is adjusted according to a type of the solvent, affinity between the solvent and the solid, an amount of the solvent, or fluidization conditions.

5. The method of claim 1, wherein in process (b), the solvent is added in an amount of 10 parts by volume to 200 parts by volume with respect to 100 parts by weight of the solid.

6. The method of claim 1, wherein in process (b), a drug is further loaded in the solvent.

7. The method of claim 6, further comprising, after process (b), re-solidifying the fluidized solid and then re-fluidizing the solid by adding a second solvent thereto.

8. The method of claim 1, wherein in process (c), the shaping is performed using a method selected from the group consisting of molding, drawing, air blowing, suction, application of centrifugal force, application of a magnetic field, and a combination thereof.

9. The method of claim 1, wherein in process (c), the shaping is performed in such a way that curing simultaneously occurs.

10. The method of claim 1, wherein an aspect ratio of the microstructure shaped in process (c) is adjusted according to a degree of fluidization.

11. The method of claim 6, wherein a loading distribution of the drug in the microstructure shaped in process (c) is adjusted according to a degree of fluidization.

12. The method of claim 7, wherein a loading distribution of the drug in the microstructure shaped in process (c) is adjusted according to a degree of re-fluidization.

13. A method of manufacturing a microstructure, the method comprising:
    (a) forming a solid on a substrate, wherein the solid comprises a drug, and a biocompatible or biodegradable material;
    (b) dissolving a portion of the solid by adding a solvent thereto to fluidize the portion of the solid; and
    (c) shaping the fluidized solid;
    wherein in process (a), the solid has a solid content of 70% or more, in process (b) dissolving the portion of the solid is performed separately after the solid is formed on the substrate and in a case in which, with respect to a vertical direction of the substrate, the solid is divided into an upper solid layer and a lower solid layer based on a ½ point of the solid, in process (b), a degree of fluidization of the upper solid layer is higher than a degree of fluidization of the lower solid layer, wherein a loading distribution of the drug in the microstructure shaped in process (c) is adjusted according to a degree of fluidization.

* * * * *